Jan. 18, 1955 T. E. MOTOSE Plant Pat. 1,343
ROSE PLANT
Filed Feb. 2, 1954
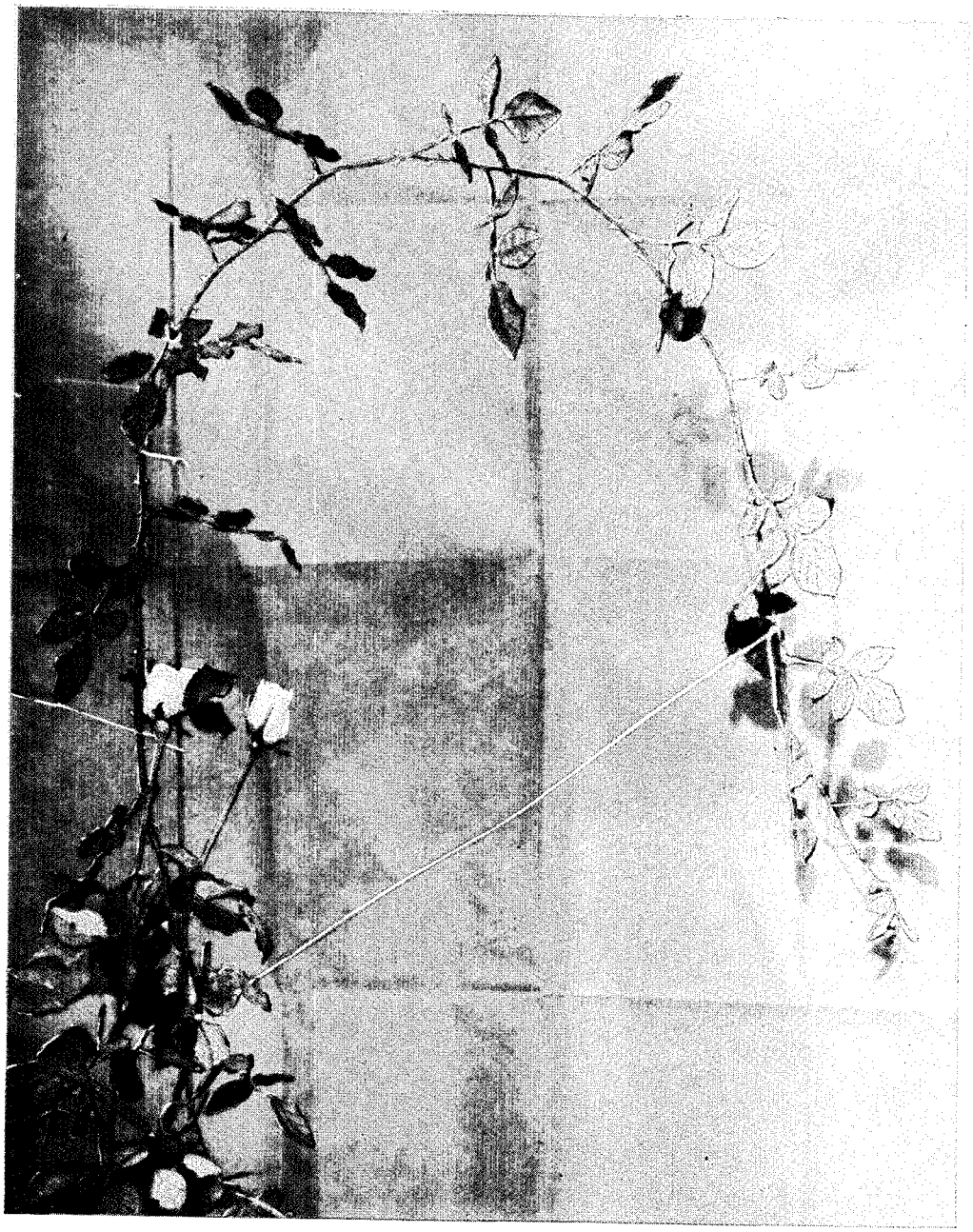
Inventor
Thomas Edison Motose United States Patent Office Plant Pat. 1,343

Patented Jan. 18, 1955

1,343

ROSE PLANT

Thomas Edison Motose, Fairport, N. Y.

Application February 2, 1954, Serial No. 407,823

1 Claim. (Cl. 47—61)

This invention relates to a new, distinct and horticulturally useful variety of climbing hybrid tea rose plant, originating as a sport or mutation of the bush-type hybrid tea rose plant known as "Tawny Gold."

The parent rose plant named Tawny Gold is a low bush-type hybrid tea rose with short branches, originated by Mathieu P. H. Leenders and patented in 1950 (Plant Patent No. 950). The Tawny Gold bears large buff-yellow bloom with orange-buff colored center and lemon-chrome color toward the base.

The new climbing variety was discovered by me on one of the low-growing Tawny Gold bushes owned by me and grown outdoors by myself. The thorns, buds, flowers and foliage of this new sport are similar in general appearance to those of the bush-type parent. The major difference between the two is that the Tawny Gold is not a climber and the new sport is a vigorous climbing variety.

This new variety is characterized as to novelty by the combination of the following traits and characteristics: (*a*) long climbing canes; (*b*) tendency to produce hybrid tea type blooms on medium and long stems more frequently than most climbing roses; (*c*) very sweet fruity fragrance; (*d*) ability to survive the extremes of temperatures in northern gardens on equal footing with some of the hardier bush-type hybrid tea rose plants; and (*e*) buff-yellow flower with orange-buff central petals and lemon-chrome shaded base similar to the bloom of its parent.

The above characteristics and traits, particularly the climbing habit, have been found to hold true through succeeding asexual propagations by the usual methods of cuttings, graftings and buddings, and are established.

The terms "climber," "climbing variety" and any noun preceded by the word "climbing" are used herein in the sense universally recognized by botanists and horticulturists: any plant that produces long canes, stems or branches that requires a tall support to keep it above the ground and which requires the aid of its tendrils if it possesses such members, or man-made articles such as strings and wires if there are no tendrils, to keep it attached to such support; or any plant that has an ability to crawl up or over a gently sloping roof, or push its long canes, branches or stems into, and entwine with, the branches of neighboring trees. The term "climbing habit" herein used refers to the ability or growing habit of such plant.

The accompanying photograph taken in Fairport, N. Y., in June 1953, is that of one of the numerous asexually reproduced plants of the new sport climber.

The place where, and the duration of, observations made for the specific purpose of compiling data on the various characteristics of the new variety of rose plant: Fairport, N. Y., beginning from the time of the discovery of the new sport through many asexual propagations.

The color terminology used herein is in accord with Ridgway's Color Standard and Nomenclature where indicated by plate number, otherwise with general dictionary meaning.

The following is a detailed description of the new variety of rose plant, the subject of this application:

(*a*) *Parentage.*—A climbing sport of the bush-type hybrid tea rose plant named Tawny Gold.

(*b*) *Botanic classification.*—A climbing hybrid tea rose plant belonging to the genus Rosa.

(*c*) *Horticultural and commercial classification.*—A climbing hybrid tea rose.

(*d*) *Place where asexually reproduced.*—Fairport, N. Y.

(*e*) *Methods of asexual reproduction used in this case.*—Buddings, cuttings and graftings. Multiflora rootstocks were used in budding the first discovered wood; the second crop was budded on *Rosa manettii* stocks. The accompanying picture is that of the new sport budded on Manettii stock and is a part of the second crop.

(*f*) *Flowering habit.*—Its habit is recurrent with long blooming periods.

(*g*) *Flower bud.*—Its size before calyx breaks is medium; its form is pointed; its color before calyx breaks is Scheele's Green (Plate 6); its sepals are long and branched, colored Scheele's Green on the outside and lighter green inside; its calyx is shaped "apple," aspect smooth; its color after calyx breaks is Orange (Plate 3) where petal surface is exposed; its peduncle is long and Lettuce Green (Plate 5).

(*h*) *Opening.*—The flower buds open very well.

(*i*) *Flower.*—Its size is large, measuring from 4 to 5½ inches in diameter on the average, and frequently exceeding the five and half inches; it is borne singly as a rule on medium and long stems; its form is high-centered at the early stage of bloom, becoming open-centered when fully blown; its petalage is double and the average number of petals under normal conditions is 25; its color when sepals first break is Orange (Plate 3), when petals begin to unfurl is Capucine Orange (Plate 3), when fully open are Buff-Yellow (Plate 4) with occasonal faint pink shade on the outer petals and always with Orange-Buff color (Plate 3) toward the central part of the bloom; the color of the base of petals is Lemon-Chrome (Plate 4) and that of the under surface of the larger ones is Apricot Yellow (Plate 4); its tonality at the end of first, second and, very frequently, third day of bloom is about the same, i. e., Buff-Yellow (Plate 4) outer petals and Orange-Buff (Plate 3) inner petals; after the 4th day of bloom its colors become gradually lighter.

(*j*) *Petal.*—Its texture is smooth; its thickness is slightly greater than the average petal of hybrid tea roses; its form is oval; its arrangement is informal; its appearance is silky; its persistence is semi-clinging.

(*k*) *Genital organs.*—Its anthers are many, medium in size and light Orange Yellow in color (Plate 3); its filaments are medium in length and Maize-Yellow in color (Plate 4); its pollen is pale Yellow Orange (Plate 3); its stigmas are light Orange Yellow (Plate 3); its styles are medium in length and columnar in appearance; and its ovaries are fully enclosed as a general rule, but occasionally just partly.

(*l*) *Foliage.*—Its formation is a compound of 5 to 7 leaflets; its size is medium; its quantity is average; the shape of the leaflet is of the general oval-pointed pattern, but resembles in appearance to the leaf of Ilex opaca (without the sharp points) when seen from the distance because of its "waved" and "serrated" edges; its ribs and veins are conspicuous; its texture is leathery; its colors when young are Oil-Green (Plate 5) with Oxblood Red (Plate 1) shade with little or no difference on the obverse and reverse sides, and when mature are Forest-Green (Plate 17) on the upper side and light Bice Green (Plate 17) on the underside; its edges are "waved" and serrated; and its stipules are smooth.

(*m*) *Wood.*—Its size is large; its color is a light Bice Green (Plate 17) with a slight overcast of Oxblood Red (Plate 1) when young, a Calliste Green (Plate 6) and occasionally Apple-Green (Plate 17) when half mature, and dull green with brownish streaks and areas when old; its bark is smooth when young and half mature, but roughens a little when mature.

(*n*) *Thorns.*—Its size is medium; its form is narrow and hooked downward; its quantity is little above the average for hybrid tea variety; its color varies from a faint pinkish color when young to brown when old.

(*o*) *Prickles and short needles.*—Their size is very small and their quantity few.

(*p*) *Plant as a whole.*—Its form is very tall and well branched; its height or length often exceeds 20 feet, although its bush-type parent rarely exceeds 3 feet; its growth is free and vigorous; and its leaves and canes are very resistant to mildew in the normal weather condition in Fairport, N. Y.

(*q*) *Asexual reproduction.*—Numerous tests have shown that the differentiating characteristics and traits of this new variety of rose plant, especially the climbing habit and vigor of growth, are thoroughly established and hold true through succeeding asexual propagations.

I claim:

A new and distinct variety of rose plant substantially as described and illustrated, characterized as to its novelty by its similarity to its parent bush-type hybrid tea rose Tawny Gold in respect to its leaves, buds and flowers, but greatly different therefrom by its exceedingly vigorous climbing habit of growth.

No references cited.